United States Patent [19]

Min-Jenn

[11] Patent Number: 4,877,963
[45] Date of Patent: Oct. 31, 1989

[54] CONTAINER FOR STORING AND STERILIZING A KITCHEN-USE CHOPPING BOARD

[76] Inventor: Liaw Min-Jenn, 9 Floor, No. 1291, Cherng-Der Rd., Taipei, Taiwan

[21] Appl. No.: 207,237
[22] Filed: Jun. 16, 1988
[51] Int. Cl.$^4$ ............................................. A61L 3/00
[52] U.S. Cl. ............................ 250/455.1; 250/504 R; 422/24
[58] Field of Search ............. 250/453.1, 455.1, 504 R; 422/24

[56] References Cited

U.S. PATENT DOCUMENTS

| | | | |
|---|---|---|---|
| 2,245,762 | 6/1941 | Stefani et al. | 250/455.1 |
| 2,253,251 | 8/1941 | Selig | 250/455.1 |
| 2,587,131 | 2/1952 | Ficken | 250/455.1 |
| 2,822,476 | 2/1958 | Osgood | 250/455.1 |
| 4,412,134 | 10/1983 | Herold et al. | 250/455.1 |
| 4,786,812 | 11/1988 | Humphreys | 250/455.1 |

Primary Examiner—Carolyn E. Fields
Assistant Examiner—John A. Miller
Attorney, Agent, or Firm—Notaro & Michalos

[57] ABSTRACT

A container in which a kitchen-use chopping board can be stored and sterilized, comprises a hollow casing having a fixed casing body and a movable casing body. A holding plate, a water collecting case, a micro-switch, a circulation fan, a sterilizing/heating lamp, a net cover and other fittings are mounted in the casing. At the time when the chopping board is being placed on the holding plate, it will be caused to descend and touch with the micro-switch to further activate the functioning of the circulation fan and the heating lamp, so as to improve the sanitary condition of the chopping board.

3 Claims, 4 Drawing Sheets

CONTAINER FOR STORING AND STERILIZING A KITCHEN-USE CHOPPING BOARD

BACKGROUND OF THE INVENTION

This invention relates to a container, in which a kitchen-use chopping board can be kept and sterilized, particularly a container which is, apart from being used as a container for a chopping board after it has been utilized, has a sterilizing effect that can effectively get rid of germs and moisture on the chopping board, so as to improve the sanitation condition of the chopping board.

It is commonly realized that sanitary cooking utensils and facility are main factors essential for good health. Judging by the present successful sales of advanced sanitation equipment and cooking utensils, how important the attention paid by modern families in improving the sanitation condition of cooking facilities in their household can readily be understood. For instance, a dish dryer is utilized to dry dishes and bowls after they have been used to serve food. On the other hand, a case-shaped rice container is mainly used for keeping rice and for preventing it from being damaged by cockroaches or other germ-carrying insects. From these instances, it can be seen that modern families are willing to improve the sanitation standard of their kitchen facility at a costly expense to ensure the good quality of the food and drinks they serve. However, no substantial means have ever been provided for the keeping and sterilization of a kitchen-use chopping board which is a utensil most frequently used, and where germs are most easily reproduced. Whether a chopping board has been thoroughly cleaned or not is the only way by which people will usually judge its sanitation condition, though cleaning by water will certainly not be able to sterilize the germs contained therein. Moreover, a large quantity of germs will be reproduced by minced meat which can stick to seams of a chopping board, if it is not thoroughly cleaned. Although the Health Authority has requested that two chopping boards should be made available in the kitchen, one for chopping raw food and the other for chopping cooked food, only a few families will act as requested. Even though two chopping boards are really found to be available in a kitchen, it is still impossible to guarantee that these chopping boards will be maintained up to the required sanitation standard.

In view of the forementioned defects, the inventor started to devote himself in researching a container, in which a chopping board can be kept and sterilized after use, so that the sanitation condition of the chopping board can be greatly improved when it is used by people for a second time. After having gone through a series of research and testing, he managed to successfuly present this invention.

SUMMARY OF THE INVENTION

It is, therefore, one primary object of the present invention to provide a container, which will provide a fixed space in which a chopping board can be kept after use and a sterilization process can also be provided within the same space by means of having a sterilization/heating device installed therein to effectively get rid of the germs and moisture which stick to on the chopping board.

A further object of the present invention is to provide a container, which can be closed by a cover body to prevent germ carrying insects from crawling into the container to pollute the chopping board.

A still further object of the present invention is to provide a container, in which a fan is used to cause the heated temperature to produce a better air circulation, so as to improve its drying effect.

A still further object of the present invention is to provide a container, which provides a convenient means of assembling and replacing of its damaged spare parts.

A still further object of the present invention is to provide a container, which will automatically provide the functions of sterilization and heating within a time which is set beforehand.

These and other objects and advantages of the present invention will become apparent from the following description taken in conjunction with the accompanying drawings.

DESCRIPTION OF THE PREFERRED EMBODIMENT

Figure 1:
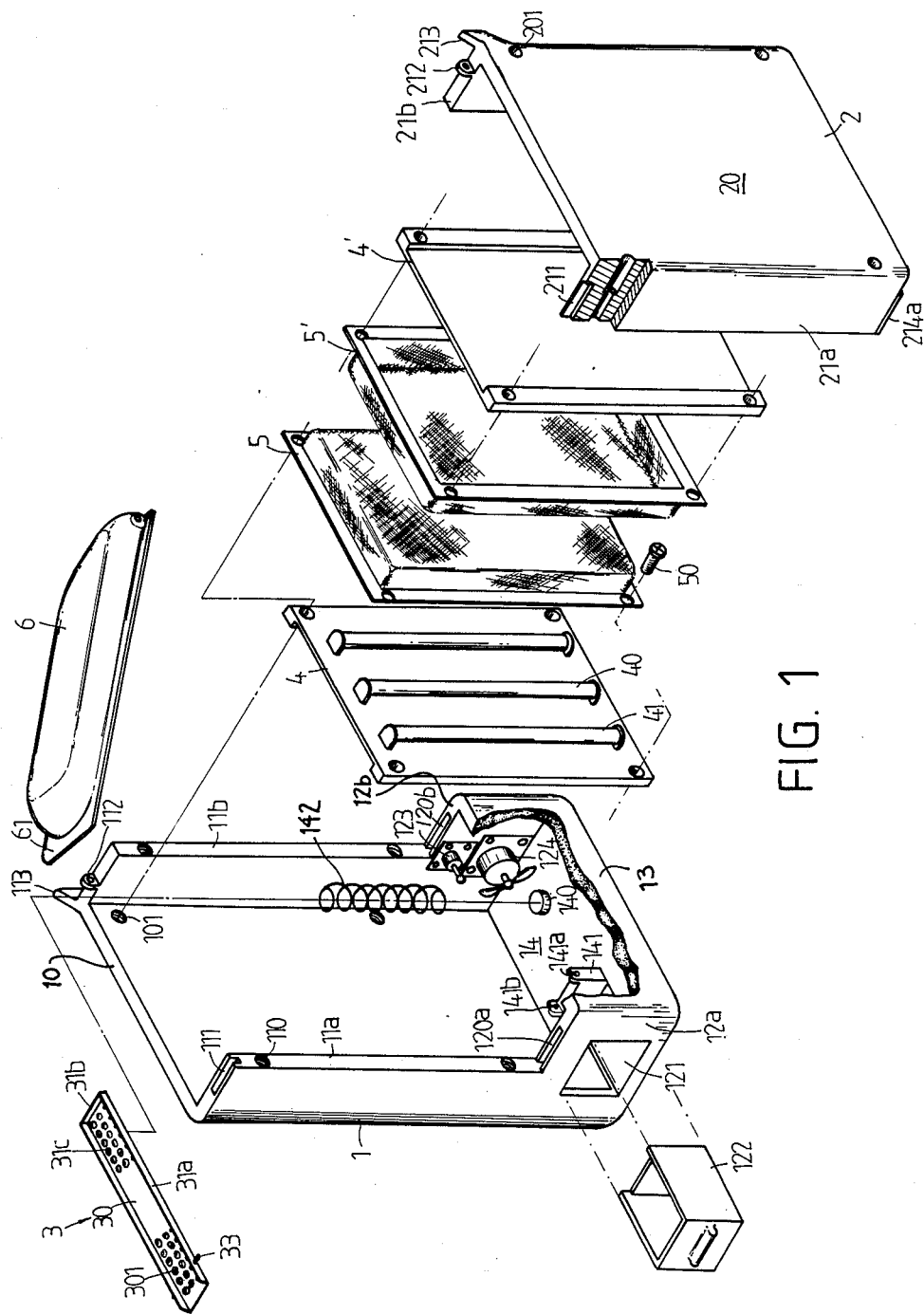
FIG. 1 is a solid segmentation drawing of a container according to the present invention.

As is shown in FIG. 1, it can be seen that the present invention is integrally formed into a hollow casing body by the assembly of a fixed casing body 1 and a movable casing body 2. In the interior of the hollow casing body various major spare parts are set beforehand. The kitchen-use chopping board will then be placed inside the formentioned hollow casing body and its drying and sterilizating effects will be achieved through the operation of its various major and component parts.

As shown in the drawings, a fixed casing body 1 is integrally formed by a horizontal long circumferential wall 10, a pair of longitudinal long circumferential walls 11a, 11b, a pair of longitudinal short walls 12a 12b, a horizontal short circumferential wall 13 and a base 14, wherein the horizontal long circumferential wall 10 and the longitudinal long circumferential wall 11a are of the same height and the aforementioned longitudinal long circumferential walls 11a 11b are formed by bending and extending from the two lateral sides of the horizontal long circumferential wall 13, while the short longitudinal circumferential walls 12a 12b are of the same height as that of horizontal short circumferential wall 13 and are formed by extending from the lower part of the longitudinal long circumferential walls 11a 11b. A screw hole 101 of a considerable depth is set beforehand at the corner position of the interior of the horizontal long circumferential wall 10; another screw hole 110 of a considerable depth is also set beforehand at each of the upper and lower ends of the opening edge of the longitudinal long circumferential wall 11a. A long strip shaped sandwiching groove 111 is provided at the top and close to the exterior lateral side of the longitudinal long circumferential wall 11a, while a joining ear 112 is set beforehand at the top plane which is close to the interior lateral side of the longitudinal long circumferential wall 11b. Wall 11b also has a ratchet-shaped stopper block 113 extended horizontally outward from the corner of the horizontal long circumferential wall 10.

At the top plane of the two walls 12a 12b, are grooves 120a and 120b. A long square-hole 121 is set beforehand at the lower end of wall 11a close to the exterior lateral side of the longitudinal short circumferential wall 12a, where a water collection case 122 will be received. A micro-switch 123 and a circulation fan 124 are separately set at the upper and the lower end of the inner surface of the interior lateral side of the short circumferential wall 12b. A fixed convex stud 140 and the fixed seat of a holding plate 141 are set beforehand on the base. The fixed convex stud 140 tightly holds the lower end of a compression spring 142 and the two lateral sides of the fixed seat of the holding plate 141 have two joining groove holes 141a 141b. Both the forementioned fixed convex stud 140 and the fixed seat of the holding plate 141 are used to support a long strip-shaped holding plate 3 which is placed thereon. The forementioned holding plate 3 comprises a plate plane 30, on which a certain number of small convex studs 301 are set beforehand. Three edge frames 31a, 31b, and 31c located at three peripheral sides of the plate plane 30 which are rigidly fixed to the the plate plane 30. A convex stud 32 which is fixed to the upper end of the compression spring 142 and two joining pins 33 which are separately set at the two lateral sides 31a 31c of the long edge frame and which are seated in holes 141a and 141b, secure the plate 3 to base 14.

Figure 2:
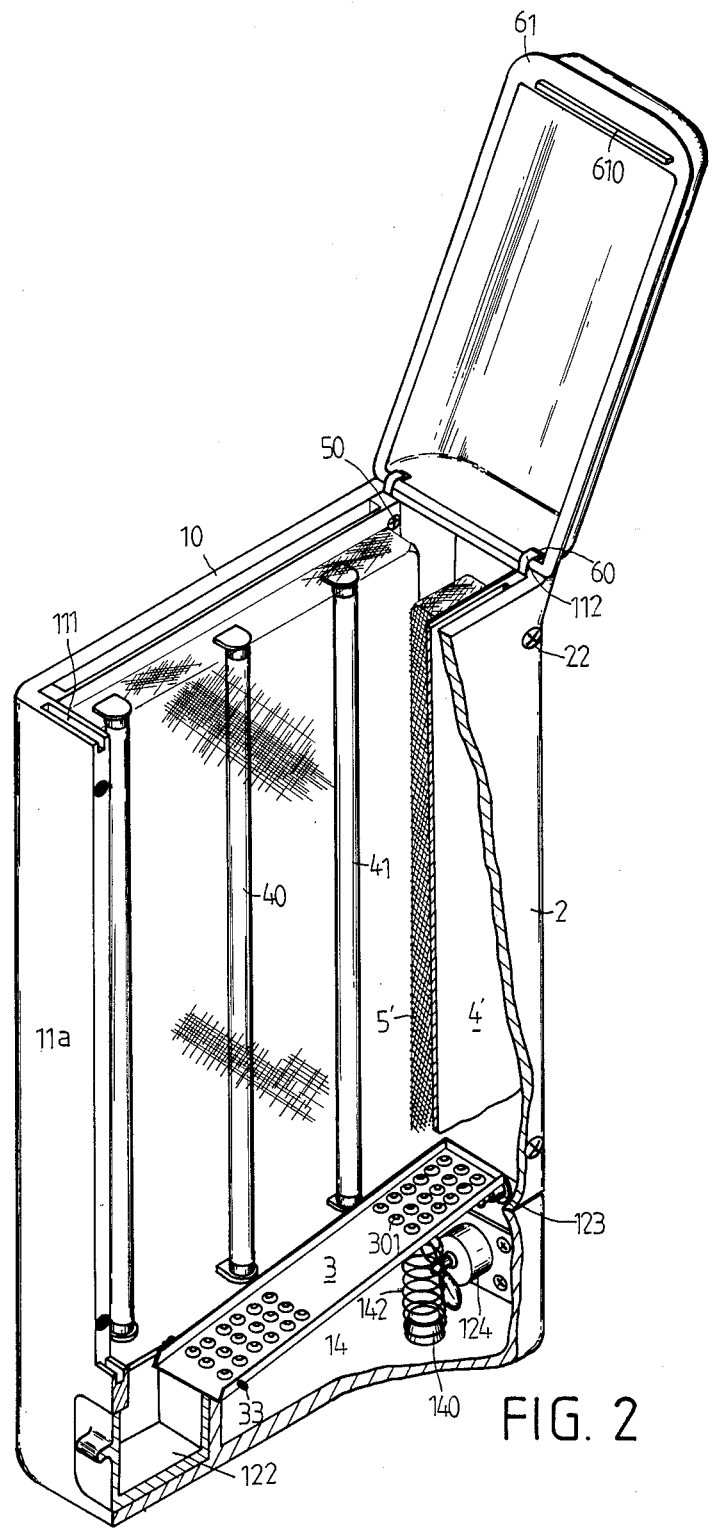
FIG. 2 is a solid cross-section drawing according to the present invention.

As shown in FIGS. 1 and 2, a fixing plate 4 is utilized to tightly fix an ultraviolet lamp tube 40 for sterilization purpose, a the heating/drying tube 5 and a net cover 41 being utilized to protect the forementioned lamp tube 40 and the heating/drying tube 41. Plate 4 is tightly secured by screws 50 screwed into the screw holes 101.

Figure 3:
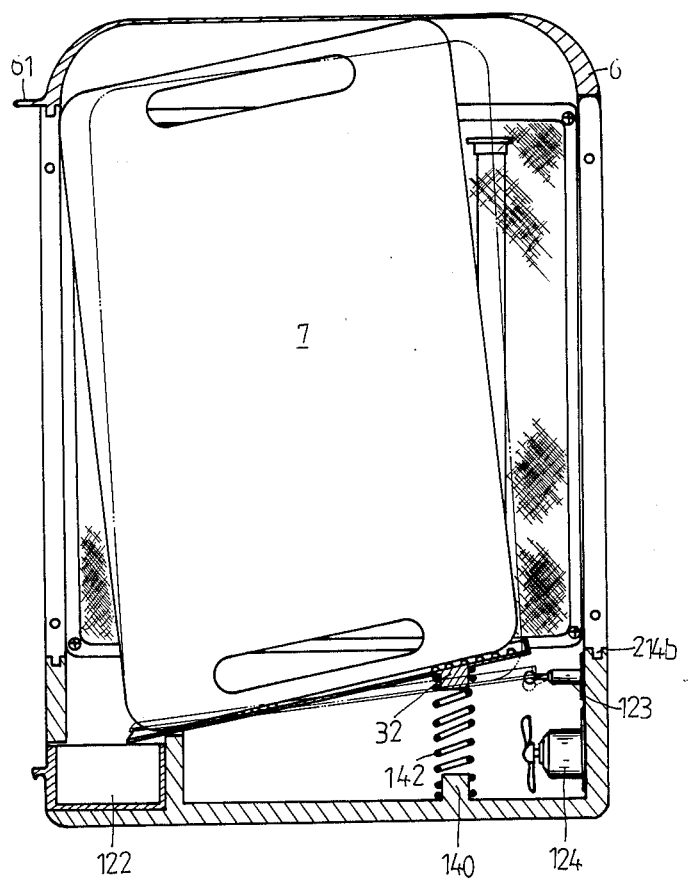
FIG. 3 shows a longitudinal sectional elevation of the container during operation.
Figure 4:
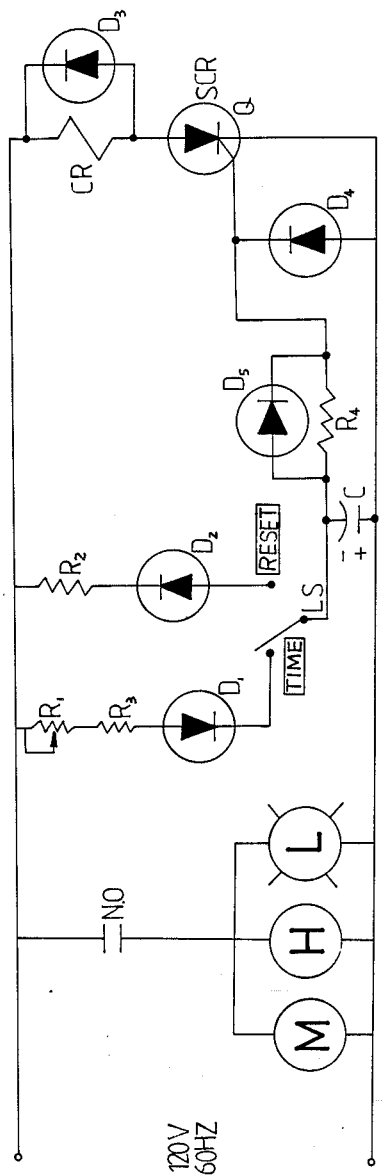
FIG. 4 is a circuit drawing.

Referring to FIGS. 1 and 2, a movable casing body 2 is integrally formed by a horizontal long circumferential wall 20 and a pair of longitudinal long circumferential walls 21a and 21b. Holes 201 are preset at the four corners of the horizontal long circumferential wall 20 and a long-hole shaped sandwiching groove 211 is preset at the top plane which is rather close to the exterior lateral side of the longitudinal long circumferential wall 21a which also has a strip-shaped convex tenon 214a preset at its lower end. Also set at its lower end is a strip shaped convex tenon 214b, (see FIG. 3). Extending from the corner of the horizontal long circumferential wall 20 is a ratchet shaped stopper block 213. A described, a fixing lamp tube 40', a fixing plate 4' of a heating tube 41' and a protective net cover 5' are tightly screwed in the interior of the horizontal long circumferential wall 20 of movable casing body 2. The pair of sandwiching tenons 214a 214b of the longitudinal long circumferential walls 21b 21b are sandwiched inside the sandwiching grooves 120a 120b which are located at the top plane of the pair of longitudinal short circumferential walls 12a 12b of the aforementioned fixed casing body 1. By means of a long screw bolt 22 through the through hole 201 of the movable casing body 2 and screwed into the screw hole 110 of the fixed casing body 1, the movable casing body 2 will then be firmly joined to one of the lateral sides of the fixed casing body 1, so as to form a hollow casing body. As for the joining ears 112 212 which are preset at the upper part of the fixed casing body 1 and the movable casing body 2, they are designed to be housed in a groove 60 which is preset at the interior lateral side at the end of a cover body 6 and, the long-hole shaped sandwiching grooves 111 211 which are preset at the top plane of the front edge of the fixed casing body 1 and the movable casing body 2 are provided for the setting of the convex tenon 610 which is set at the lower end of the front edge tongue 61 of the cover body. The rachet shaped stopper blocks 113 213 which are set at the fixed casing body 1 opposing the lateral side of the movable casing body 2 are used to restrain the maximum opening extent of the cover body 6 after it has been opened. Accordingly, the various spare and component parts of the present invention can be assembled to become a model as shown in FIG. 2 by following the forementioned procedures. As for its embodiment, please refer to FIG. 3, wherein the chopping board can, after it has been thoroughly cleaned, be placed into the hollow part of the container and let the bottom part of the chopping board be placed onto the holding plate. At this time, any water droplet will naturally fall down through the space between the small convex studs of the plate plane of the slanting holding plate into the water collection case. In addition, the holding plate will, being pressed by the weight of the chopping board, naturally exert a downward pressure onto the compression spring 142 and will also move downwardly. During the course of its downward moving, once the end of the holding plate gets in touch with the micro-switch 123, the forementioned micro-switch 123 will, as shown in FIG. 4, automatically switch on the circulation fan 124, the ultraviolet lamp tube 40 for sterilization purpose and the heating/drying tube 41. At the same time, the timing of sterilization and heating can be preset by the RC Circuit which is fixed inside the micro-switch 123. The circuit will be automatically cut off once the preset time is over. Therefore, after the chopping board has been cleaned up and placed inside the closing space of the casing body, within a preset time it will, in addition to being sterilized by the ultraviolet lamp tube, be also dried by the heating lamp and the circulation air current produced by the circulation fan. It will not only strengthen the drying effect to be exerted over the chopping board 7, but will also get rid of the germs contained therein, so as to ensure the sanitation condition of the chopping board.

I claim:

1. A container, in which a kitchen-use chopping board is stored and sterilized, comprising:
   a fixed casing body, which is integrally formed by a horizontal long circumferential wall, a longitudinal long circumferential wall, two longitudinal short circumferential walls, a horizontal short circumferential wall and a bottom part;
   a movable casing body, which is integrally formed by a horizontal long circumferential wall and two longitudinal long circumferential walls and is locked to one lateral side of the fixed casing body;
   a pair of fixing plates on which a lamp tube for sterilization and a lamp tube for heating purposes are rigidly fixed and, each lamp tube is separately fixed to an interior layer of the fixed casing body and the movable casing body;
   a pair of net covers, which is set at an exterior lateral side of the fixing plates and are also jointly fixed with the fixing plates into the interior layer of the fixed casing body and the movable casing body, so as to protect the forementioned lamp tube and heating tube from being damaged;
   a micro-switch, which is set at the interior layer proximate an interior lateral side of the longitudinal short circumferential wall;
   a water collection case, which is set at an aperture which is preset at the lower direction proximate an exterior lateral side of the longitudinal short circumferential wall and is removed at will;
a compression spring, the lower end of which is rigidly fixed to a convex stud which is preset at the bottom part of the fixed casing body and, the upper end of which is rigidly fixed to a convex stud which is preset at the lower direction of the plate plane of a holding plate;
a fixing seat of the holding plate, which is rigidly fixed at the bottom part of the casing body and on which a joining groove hole is set which is connected with the holding plate;
the holding plate on which a plurality of convex studs are scattered, having joining pins set at two lateral sides of its front edge to coordinate with joining groove holes set on a fixed seat of the holding plate and, each convex stud is preset at the reversed side of the plate plane being rigidly fixed with the upper end of the compression spring;
a cover body, which is housed to the top plane of the fixed casing body and the movable casing body and is closed or opened at will;
a circulation fan mounted in the fixed casing body;
the elements of the forementioned assembly cooperating such that the holding plate will be caused to descend under the weight of the chopping board when it is being put inside the casing body and placed on it to get in touch with the micro-switch to further activate the functioning of the circulation fan and the sterilization lamp tube and the heating lamp tube to sterilize and store the chopping board.

2. The container in which a kitchen-use chopping board is stored and sterilized as described under claim 1, wherein both the horizontal long circumferential walls of the fixed casing body and the movable casing body are extending toward one lateral side and having a correlatively opposing ratchet shaped stopper block which is used to limit the opening extend of the cover body.

3. The container in which a kitchen-use chopping board is stored and sterilized as described under claim 1, wherein a RC Circuit for timing purposes can be preset inside the micro-functioned switch.

* * * * *